United States Patent
Aucagne et al.

(10) Patent No.: US 9,073,969 B2
(45) Date of Patent: Jul. 7, 2015

(54) COMPOUNDS AND METHODS FOR PURIFYING PEPTIDES PRODUCED BY SOLID PHASE PEPTIDE SYNTHESIS

(75) Inventors: Vincent Aucagne, Fleury les Aubray (FR); Agnes Delmas, Orleans (FR)

(73) Assignee: CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 86 days.

(21) Appl. No.: 13/509,834

(22) PCT Filed: Nov. 16, 2010

(86) PCT No.: PCT/EP2010/067539
§ 371 (c)(1),
(2), (4) Date: May 15, 2012

(87) PCT Pub. No.: WO2011/058188
PCT Pub. Date: May 19, 2011

(65) Prior Publication Data
US 2012/0226019 A1    Sep. 6, 2012

(30) Foreign Application Priority Data
Nov. 16, 2009    (EP) .................................... 09306101

(51) Int. Cl.
| | |
|---|---|
| C07K 1/04 | (2006.01) |
| C07K 1/14 | (2006.01) |
| C07K 2/00 | (2006.01) |
| C07K 4/12 | (2006.01) |
| C07K 14/00 | (2006.01) |
| C07K 14/435 | (2006.01) |
| A61K 38/02 | (2006.01) |
| A61K 38/16 | (2006.01) |
| C07K 1/107 | (2006.01) |
| C07K 4/00 | (2006.01) |
| A61K 38/17 | (2006.01) |
| A61K 38/10 | (2006.01) |
| A61K 38/04 | (2006.01) |
| C07K 1/00 | (2006.01) |
| C07K 7/04 | (2006.01) |

(52) U.S. Cl.
CPC ................ *C07K 1/1075* (2013.01); *C07K 1/04* (2013.01); *C07K 4/00* (2013.01); *C07K 4/12* (2013.01); *C07K 2/00* (2013.01); *A61K 38/17* (2013.01); *A61K 38/16* (2013.01); *A61K 38/10* (2013.01); *A61K 38/04* (2013.01); *C07K 1/006* (2013.01); *C07K 1/14* (2013.01); *C07K 7/04* (2013.01); *C07K 14/435* (2013.01)

(58) Field of Classification Search
CPC ............ C07K 1/14; C07K 1/04; C07K 1/006; C07K 4/00; C07K 1/12; C07K 2/00; A61K 38/17; A61K 38/16; A61K 38/10; A61K 38/04; A61K 38/02
USPC ......................................................... 530/412
See application file for complete search history.

(56) References Cited

U.S. PATENT DOCUMENTS

2007/0213278 A1    9/2007   Wong et al.

FOREIGN PATENT DOCUMENTS

| GB | 1481389 | 7/1977 |
|---|---|---|
| WO | 2008/104000 | 8/2008 |

OTHER PUBLICATIONS

Funakoshi et al., Proc. Natl. Acad. Sci. USA, Biochemistry (1991) vol. 88, 6981-6985.*
Hermanson, Bioconjugate Techniques, $2^{nd}$ ed., Chapter 18 (Aug. 2008) Elsevier Inc.: London.*
Bycroft et al., J. Chem. Soc., Chem. Commun. (1993) 9, 778-779.*
Database Beilstein [Online] Beilstein Institute for Organic Chemistry, Frankfurt-Main, DE; 1983, Achmatowicz, O. et al. XP002580256.
International Search Report in PCT/EP2010/067539, dated Mar. 14, 2011.
Le Droumaguet et al., "Click Chemistry: A powerful toolf to create polymer-based macromolecular chimeras," Macromolecular: Rapid Communications, Wiley VCH Verlag, Weinheim, DE, 29:1073-1089 (2008) XP002580257.
Ten Brink et al., "Solid-phase synthesis of C-terminally modified peptides," J. Peptide Sci., 12:686-692 (2006) XP002450637.
Tornoe et al., "Peptidotriazoles on solid phase: [1,2,3]-triazoles by regiospecific copper(i)-catalyzed 1,3-dipolar cycloadditions of terminal alkynes to azides," J. Org. Chem., 67(9):3057-3064 (2002) XP002567967.

\* cited by examiner

*Primary Examiner* — Karlheinz R Skowronek
*Assistant Examiner* — Catherine Mader
(74) *Attorney, Agent, or Firm* — McAndrews, Held & Malloy Ltd.

(57) ABSTRACT

The invention relates to compounds which can be used for purifying peptides produced by solid phase peptide synthesis. In addition, the invention relates to methods for purifying peptides produced by solid phase peptide synthesis using the compounds according to the invention.

10 Claims, 4 Drawing Sheets

| Retention time | MH+ found | attributed to | MH+ calculated |
|---|---|---|---|
| 18.04 (A) | 2677.764 | 31-53 | $C_{118} H_{185} N_{39} O_{33}$ (2677.4069) |
| | 1617.802 | Ac-41-53 | $C_{73} H_{112} N_{22} O_{20}$ (1617.8495) |
| | 2393.117 | Ac-34-53 | $C_{106} H_{161} N_{33} O_{31}$ (2393.2108) |
| 23.29 (B) | 2563.040 | Ac-32-53 | $C_{114} H_{175} N_{35} O_{33}$ (2563.3163) |
| 24.80 (C) | 1461.716 | Ac-42-53 | $C_{67} H_{100} N_{18} O_{19}$ (1461.7484) |

| Retention time | MH+ found | attributed to | MH+ calculated |
|---|---|---|---|
| 17.90 (A) | 1617.802 | Ac-41-53 | $C_{73} H_{112} N_{22} O_{20}$ (1617.8495) |
| 18.17 (B) | 2393.117 | Ac-34-53 | $C_{106} H_{161} N_{33} O_{31}$ (2393.2108) |
| 22.79 (C) | 2563.221 | Ac-32-53 | $C_{114} H_{175} N_{35} O_{33}$ (2563.3163) |
| 24.18 (D) | 1461.641 | Ac-42-53 | $C_{67} H_{100} N_{18} O_{19}$ (1461.7484) |
| 25.11 (E) | 2506.315 | Ac-33-53 | $C_{112} H_{172} N_{34} O_{32}$ (2506.2949) |
| 26.09 (F) | 2926.491 | $N_3$-Tag-31-53 | $C_{125} H_{196} N_{42} O_{38} S$ (2926.4488) |
| 29.59 (G) | 1567.782 | Ac-42-53 (+106) | $C_{74} H_{106} N_{18} O_{20}$ (1567.7903) |

| Retention time | MH+ found | attributed to | MH+ calculated |
|---|---|---|---|
| 18.45 (A) | 1617.802 | Ac-41-53 | $C_{73} H_{112} N_{22} O_{20}$ (1617.8495) |
| 18.72 (B) | 2393.117 | Ac-34-53 | $C_{106} H_{161} N_{33} O_{31}$ (2393.2108) |
| 23.38 (C) | 2563.221 | Ac-32-53 | $C_{114} H_{175} N_{35} O_{33}$ (2563.3163) |
| 24.71 (D) | 1461.641 | Ac-42-53 | $C_{67} H_{100} N_{18} O_{19}$ (1461.7484) |
| 25.61 (E) | 2506.315 | Ac-33-53 | $C_{112} H_{172} N_{34} O_{32}$ (2506.2949) |
| 30.12 (F) | 1567.782 | Ac-42-53 (+106) | $C_{74} H_{106} N_{18} O_{20}$ (1567.7903) |

| Retention time | MH+ found | attributed to | MH calculated |
|---|---|---|---|
| 18.32 (A) | 2677.278 | 31-53 | $C_{118} H_{185} N_{39} O_{33}$ (2677.4069) |
| 22.01 (B) | 2783.509 | 31-53 (+106) | $C_{125} H_{191} N_{39} O_{34}$ (2783.4487) |

SEQUENCE LISTING

```
<160> NUMBER OF SEQ ID NOS: 1

<210> SEQ ID NO 1
<211> LENGTH: 23
<212> TYPE: PRT
<213> ORGANISM: Homo sapiens

<400> SEQUENCE: 1

Arg Gly Leu Ser Trp Thr Gly Thr Ser Arg Arg Leu Pro Trp Ser Thr
1               5                   10                  15

Trp Ser Leu Ser Arg Ser Thr
            20
```

COMPOUNDS AND METHODS FOR PURIFYING PEPTIDES PRODUCED BY SOLID PHASE PEPTIDE SYNTHESIS

The present application is filed pursuant to 35 U.S.C. 371 as a U.S. National Phase application of International Patent Application No. PCT/EP2010/067539, which was filed Nov. 16, 2010, claiming the benefit of priority to European Patent Application No. 09306101.8, which was filed on Nov. 16, 2009. The entire text of the aforementioned applications is incorporated herein by reference in its entirety.

FIELD OF THE INVENTION

The invention relates to compounds and methods for purifying peptides produced by solid phase peptide synthesis.

BACKGROUND OF THE INVENTION

Chemical synthesis of peptides is well established. In principle, two different methods are distinguished: the synthesis in solution, which is often very time consuming and therefore not useful for scientific research, and the synthesis on a solid support, which allows a fast optimization of reaction cycles. The protocols available for solid phase peptide synthesis (SPPS) are based on the Merrifield technique (Merrifield, R. B., J. Amer. Chem. Soc. 85, 1963, 2149) for synthesizing peptides with defined sequences on an insoluble solid phase. The general principle of SPPS is based on the repetition of cycles of coupling-deprotection: the free N-terminal amine of a peptide attached on a solid phase by its carboxyl end is coupled to a single N-protected amino acid unit. This unit is then deprotected, revealing a new N-terminal amine to which a further amino acid may be attached.

However, present SPPS methods produce, in addition to the target compounds (the mature peptides), a relatively large number of impurities, and particularly a large amount of immature peptides. Purification of peptides derived from solid-phase peptide synthesis (SPPS) hence requires the removal of deleted peptides (ie peptides lacking one or several amino acid residues) resulting from incomplete coupling/deprotection steps and, in a much lesser extent, other peptide co-products from racemisation or side-chain rearrangement, and of various chemical substances introduced during the deprotection or cleavage stages of an SPPS procedure. In particular, the more the peptides to be synthesized are long, the more the number of impurities and in particular the number of deleted peptides is. Therefore, an important objective of a SPPS method is to recover the target peptide alone from impurities with high speed and high yield.

It has thus been proposed to perform a capping by acetic anhydride after every coupling reaction to terminate further elongation of peptide chains of a non-target sequence and to avoid further production of deleted peptides and obtain truncated peptides. After the coupling of the final amino acid, only the peptide having a complete amino acid sequence will have an amino group at its N-terminus: this amino group can be used to purify the target peptide.

Several reports on peptide purification methods using the N-terminus amino group have been published. However, none of these methods has been able to achieve effective one-step separation; instead complicated separation processes are required.

Another method has been developed in which the target peptide alone is elongated with two extra residues (cysteine-methionine) at its N-terminus, then reacted with a solid support derivatized with a phenyl-mercury group taking advantage of the selective binding of the SH group of the cysteine. Subsequent to the separation, the methionine-peptide amide bond is selectively cleaved by BrCN to yield the target peptide (D. E. Krieger et al., Proc. Natl. Acad. Sci. U.S.A., 73, 3160 (1976)). However, this method has a limitation of being not applicable to peptides containing methionine or cysteine.

Still another method has been disclosed in which the target peptide is covalently linked to a solid support through a SH group (U.S. Pat. No. 5,648,462 and No. 5,994,588). However, this method has a limitation of being not applicable to peptides containing cysteine.

There is thus a need for further methods for purifying the peptides produced by SPPS, said methods being applicable to any type of peptides and being easy to carry out.

SUMMARY OF THE INVENTION

The inventors have found that, at the end of the SPPS, and before the step of deprotection/cleavage of the peptides from the solid phase, it is possible to tag selectively the mature peptides with a compound comprising two chemical functions separated by a linker. This compound can then be used for purifying the mature peptides from the other end-capped truncated peptides (immature peptides) by reacting said compound with a particular solid phase according to the invention. The invention thus relates to a compound having general formula (I):

$$X_1\text{-}L\text{-}X_2 \qquad (I)$$

wherein:
$X_1$ is selected from the group consisting of $-N_3$ or $-C\equiv CH$,
L represents a linker separating $X_1$ and $X_2$,
$X_2$ is selected from the group consisting of the compounds having general formula (A), (B) and (C):

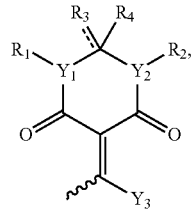

(A)

wherein:
$Y_1$ and $Y_2$ independently represent $-CH-$ or $-N-$,
$Y_3$ represents $-OH$ or a leaving group,
$R_1$ and $R_2$ independently represent $-H$, $-CH_3$, or a $C_2$-$C_5$ alkyl,
the dotted line is present or not,
when the dotted line is present, $R_3$ is O and $R_4$ is absent,
when the dotted line is not present, $R_3$ and $R_4$ represent $-CH_3$;

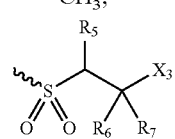

(B)

wherein:
$R_5$ represents $-H$ or an Electron-Withdrawing Group,
$R_6$ and $R_7$ independently represent $-CH_3$ or $-H$,
$X_3$ is a carbamate precursor;
and

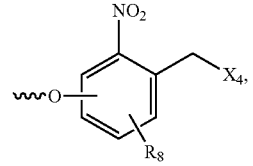

(C)

wherein:
$R_8$ represents $-O-CH_3$ or $-H$, and
$X_4$ is a carbamate precursor.

The invention also relates to a method for purifying a peptide produced by solid-phase synthesis, said method comprising the steps of:
- (a) obtaining a mixture of mature peptides having a free N-terminal amino group and immature end-capped peptides, wherein said mature and immature peptides have their side chains protected and are covalently bound to a solid phase;
- (b) contacting the mixture of step (a) with a compound having general formula (I) according to the invention, wherein said step of contacting the mixture obtained from step (a) with a compound having general formula (I) results in the formation of a covalent link between the mature peptide and the compound having general formula (I) by reaction of the free N-terminal amino group of the mature peptide with $X_2$,
- (c) subjecting the mixture obtained from step (b) to an acid treatment to cleave the peptides from the solid phase,
- (d) contacting the peptides obtained from step (c) with a solid support capable of reacting with $X_1$, said step resulting in the formation of a stable covalent bond between the solid support and the mature peptides,
- (e) washing the solid support obtained from step (d) to remove immature end-capped peptides,
- (f) obtaining purified mature peptides by liberating them from the solid support by cleaving the covalent bond between $X_2$ and the mature peptides under a condition selected from the group consisting of:
  - i. nucleophilic condition when $X_2$ is (A),
  - ii. alkaline condition when $X_2$ is (B), and
  - iii. UV irradiation when $X_2$ is (C).

The invention still relates to the use of a compound having general formula (I) according to the invention for purifying a peptide produced by solid-phase synthesis.

DETAILED DESCRIPTION OF THE INVENTION

As shown in FIG. 1, the general principle of the invention is the following: thanks to the chemical group $X_2$, the compound according to the invention can specifically react with the free N-terminal amino group of the mature peptides to form a covalent bond, said covalent bond being specifically cleavable under particular conditions. After deprotection/cleavage from the solid phase, the peptides are then put into contact with a solid support capable of specifically reacting with $X_1$, said reaction leading to the formation of a completely stable covalent bond between the mature peptides and said solid support. Since the reaction between $X_1$ and the solid support (reaction between an azide and an alkyne, preferably catalyzed by copper (I) salts, or reaction between an azide and a phosphine) is highly chemoselective and thus cannot occur with the chemical functions present on the amino acids constituting the peptides (amino acids do not comprises azide, alkyne or phosphine functions), this method presents the advantage of being applicable to any type of peptides, whatever its amino acid content. In addition, this method is very quick and easy to carry out.

The invention thus relates to a compound having general formula (I):

$$X_1\text{-}L\text{-}X_2 \quad (I)$$

wherein:
- $X_1$ is selected from the group consisting of —$N_3$ or —C≡CH,
- L represents a linker separating $X_1$ and $X_2$,
- $X_2$ is selected from the group consisting of the compounds having general formula (A), (B) and (C):

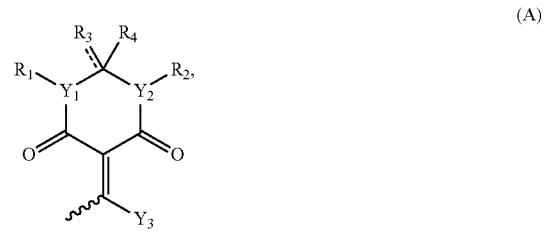
(A)

wherein:
- $Y_1$ and $Y_2$ independently represent —CH— or —N—,
- $Y_3$ represents —OH or a leaving group,
- $R_1$ and $R_2$ independently represent —H, —$CH_3$, or a $C_2$-$C_5$ alkyl,
- the dotted line is present or not,
- when the dotted line is present, $R_3$ is O and $R_4$ is absent,
- when the dotted line is not present, $R_3$ and $R_4$ represent —$CH_3$;

(B)

wherein:
- $R_5$ represents —H or an Electron-Withdrawing Group,
- $R_6$ and $R_7$ independently represent —$CH_3$ or —H,
- $X_3$ is a carbamate precursor;

and

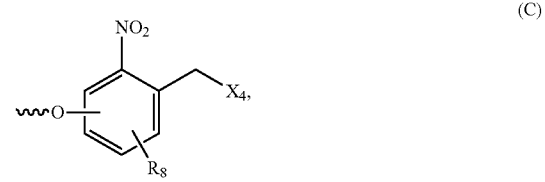
(C)

wherein:
- $R_8$ represents —O—$CH_3$ or —H, and
- $X_4$ is a carbamate precursor.

According to the invention, said linker L of the compound having general formula (I) according to the invention typically separates $X_1$ and $X_2$ by at least one atom, particularly by 1 to 30 consecutive atoms, more particularly by 1 to 20 consecutive atoms, still particularly by 1, 2, 3, 4, 5, 6, 7, 8, 9 or 10 consecutive atoms. Typically, said linker L of the compound having general formula (I) according to the invention is selected from the group comprising:
- —$(CH_2)_n$—,
- —$CH_2$—$(CH_2$—O—$CH_2)_n$—$CH_2$—,
- —Ar—,
- —$(CH_2)_n$—Ar—,
- —$CH_2$—$(CH_2$—O—$CH_2)_n$—$CH_2$—Ar—,
- —$(CH_2)_n$—O—Ar—,
- —$CH_2$—$(CH_2$—O—$CH_2)_n$—$CH_2$—O—Ar—, and
- —$CH_2$—$(CH_2$—O—$CH_2)_n$—Ar—, wherein "n" is 1, 2, 3, 4, 5, 6, 7, 8, 9, 10 or more, and wherein Ar represents an aryl group having the following formula:

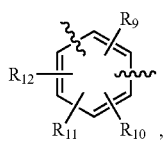

wherein $R_9$, $R_{10}$, $R_{11}$ and $R_{12}$ independently represent H, —$CH_3$, —O—$CH_3$, —$NO_2$, or an halogen atom typically selected from the group consisting of F, Cl, Br and I.

Typically, according to the invention, said compound of general formula (A) is selected from the group comprising:

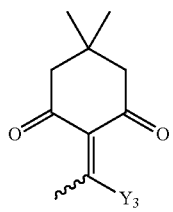 and 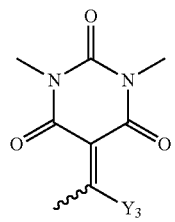

wherein $Y_3$ represents —OH or a leaving group.

According to the invention, when $Y_3$ is a "leaving group", said leaving group can be any group able to depart with a pair of electrons in heterolytic bond cleavage. In particular, when $Y_3$ is a "leaving group", $Y_3$ is typically selected from the group comprising —$OR_{13}$ and $N(R_{13})_2$, wherein $R_{13}$ represents $CH_3$ or a $C_2$, $C_3$, $C_4$ or $C_5$ alkyl.

According to the invention, by "Electron-Withdrawing Group" or "EWG" it is meant any chemical group able to draw electrons away from its adjacent atoms through inductive or mesomeric effect. Typically, an Electron-Withdrawing Group according to the invention is selected from the group comprising the Electron-Withdrawing groups having the following formulae:

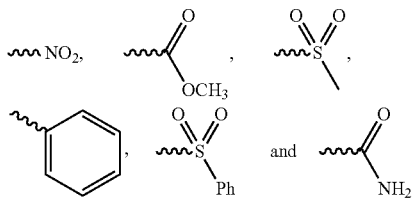

According to the invention, by "carbamate precursor", it is meant any chemical group able to react with an amine to form a carbamate function. A particular carbamate precursor according to the invention has the general formula (II):

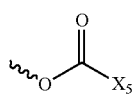

(II)

wherein $X_5$ is a leaving group.

According to the invention, when $X_5$ is a "leaving group", said leaving group can be any group able to depart with a pair of electrons in heterolytic bond cleavage. In particular, said leaving group $X_5$ is typically selected from the group comprising:

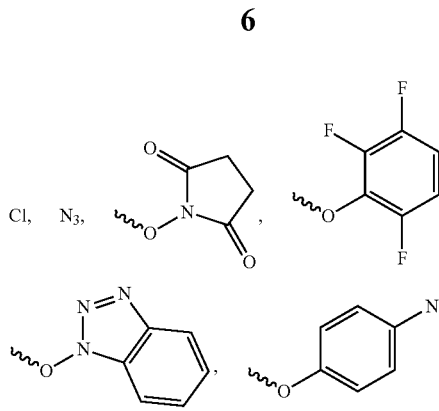

In a particular embodiment, said compound of general formula (B) is selected from the group comprising:

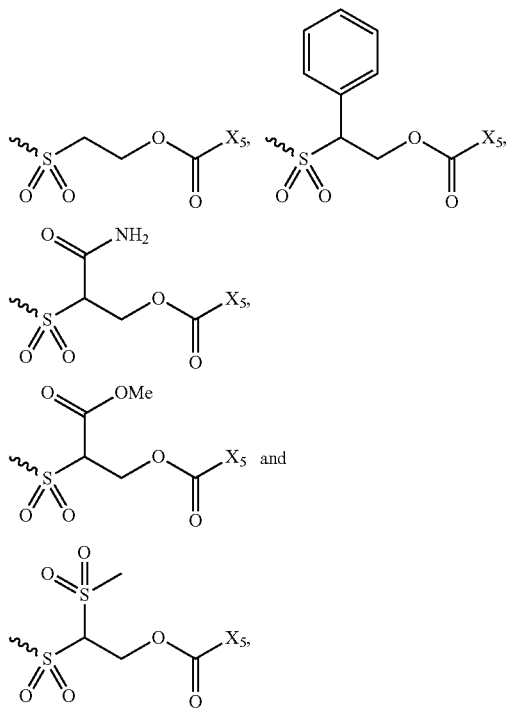

wherein $X_5$ is as defined previously.

In another particular embodiment, said compound of general formula (C) is selected from the group comprising:

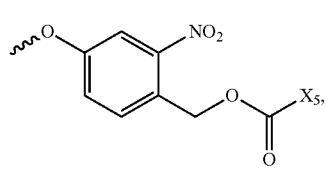

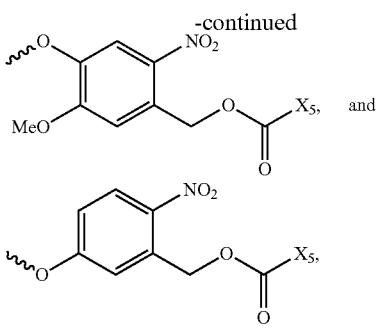

wherein $X_5$ is as defined previously.

In one embodiment, said compound of general formula (C) according to the invention is not

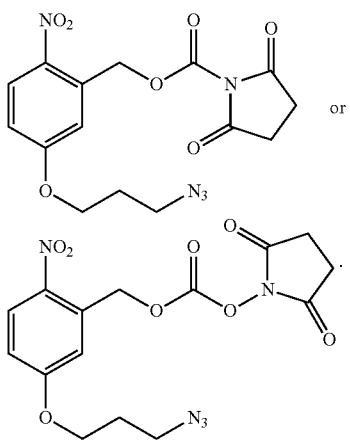

In another embodiment, said compound of general formula (C) according to the invention is not

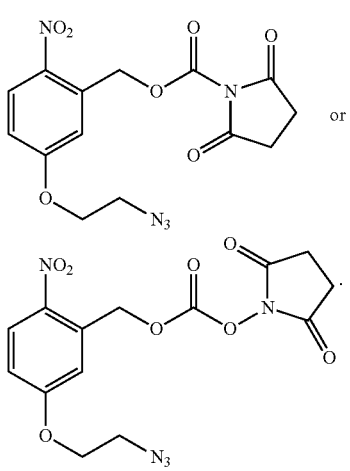

The synthetic pathway to the compound according to the invention is not subject to any limitation. Typically, the compounds of general formula (A) according to the invention are obtained from the C-acylation of 1,3-dimethyl barbituric acid or 5,5-dimethyl-1,3-cyclohexanedione under standard procedures. Typically, the compounds of general formula (B) according to the invention are obtained from 2-mercapto ethanol, which is S-alkylated or arylated, then oxidized to the sulfone, to give an alcohol that is further converted into a carbamate precursor of general formula (II) under standard conditions. Typically, the compounds of general formula (C) according to the invention are obtained from a benzylic alcohol that is further converted into a carbamate precursor of general formula (II) under standard conditions.

The invention also relates to a method for purifying a peptide produced by solid-phase synthesis, said method comprising the steps of:

(a) obtaining a mixture of mature peptides having a free N-terminal amino group and immature end-capped peptides, wherein said mature and immature peptides have their side chains protected and are covalently bound to a solid phase;

(b) contacting the mixture of step (a) with a compound having general formula (I) according to the invention, wherein said step of contacting the mixture obtained from step (a) with a compound having general formula (I) results in the formation of a covalent link between the mature peptide and the compound having general formula (I) by reaction of the free N-terminal amino group of the mature peptide with $X_2$, (c) subjecting the mixture obtained from step (b) to an acid treatment to cleave the peptides from the solid phase, (d) contacting the peptides obtained from step (c) with a solid support capable of reacting with $X_1$, said step resulting in the formation of a stable covalent bond between the solid support and the mature peptides, (e) washing the solid support obtained from step (d) to remove immature end-capped peptides, (f) obtaining purified mature peptides by liberating them from the solid support by cleaving the covalent bond between $X_2$ and the mature peptides under a condition selected from the group consisting of:
   i. nucleophilic condition when $X_2$ is (A),
   ii. alkaline condition when $X_2$ is (B), and
   iii. UV irradiation when $X_2$ is (C).

According to the invention, said "mixture of mature peptides having a free N-terminal amino group and immature end-capped peptides, wherein said mature and immature peptides have their side chains protected and are covalently bound to a solid phase", is obtained after any SPPS method. In particular, said immature peptides having their N-terminal modified by a capping group are typically capped with an acetyl-group if the capping has been performed with acetic anhydride, or with a propionyl group, a 4-nitrophenyl group, a 2,4-dinitrophenyl group or with 2,6-dinitrophenyl group. In addition, the protection of the side chains of the mature and immature peptides during the SPPS can be performed by any method known by the skilled person, such as for example using the Boc, tBu, Trt, Mtt, Mmt, Pbf, Pmc, Tos, Bzl, Z, Troc, Pac, Alloc, All, Dde, Acm protecting groups. Concerning the nature of the solid phase used in SPPS, any appropriate solid phase can be selected by the skilled person. Examples of solid phases commonly used in SPPS are polystyrene-divinylbenzene copolymers, eventually substituted by PEG chains (Tentagel, Argogel, Novagel), cross-linked polyacrylamide resins or cross-linked PEG polymers such as PEGA, ChemMatrix™.

The mature peptides obtained after a SPPS are thus mixed with many kinds of impurities.

According to the invention, by "mature peptides" it is meant either several copies of a same mature peptide or several copies of different mature peptides obtained by combinatorial chemistry on solid phase.

According to the invention, said step (b) of contacting the mixture of step (a) with a compound having general formula (I) according to the invention is typically performed by reacting said peptides bound to a solid support with an excess, typically 2, 5 or 10 equivalents of the compound having general formula (I) and an excess, typically 2, 5 or 10 equivalents of a base, typically a tertiary amine such as triethylamine or ethyl diisopropylamine in a solvent, typically dimethylformamide, N-methyl pyrrolidone or dichloromethane.

When $X_2$ is a compounds having general formula (A), the bond formed between $X_2$ and the terminal amine group of the mature peptide is of the enamine type, as typically shown in formula A':

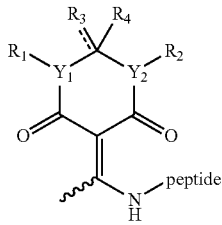

(A')

When $X_2$ is a compounds having general formula (B) or (C), the bond formed between $X_2$ and the terminal amine group of the mature peptide is of the carbamate type, as typically shown in formulae B' and C':

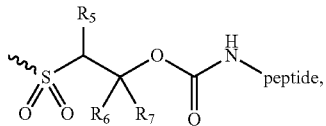

(B')

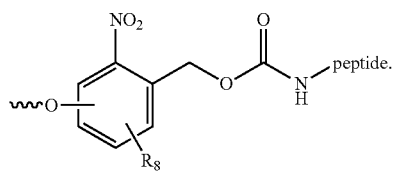

(C')

According to the invention, said step (c) of subjecting the mixture obtained from step (b) to acid to cleave the peptides from the solid-phase support, is typically performed by treatment with a solution of carbocation scavengers in TFA (trifluoroacetic acid) or hydrogen fluoride. A particularly suitable acid treatment according to the invention is a standard treatment with a mixture of triisopropylsilane (2.5% v/v), phenol (5% w/v) and water (5% v/v) in TFA.

Typically, suitable solid supports capable of reacting with $X_1$ according to the invention are selected from synthetic hydrophilic polymers, such as PEGA resin, ChemMatrix™ resin, SPOCC (superpermeable organic combinatorial chemistry) resin, or from natural hydrophilic carbohydrate polymers, such as agarose or sepharose. These solid supports are grafted with a compound capable of reacting with $X_1$, i.e. are grafted with a compound comprising an azide, an alkyne, a cyclooctyne or a phosphine function, to form a covalent, irreversible bond with $X_1$. Examples of solid supports grafted with a compound capable of reacting with $X_1$ according to the invention are:

when $X_1$ is C≡CH:

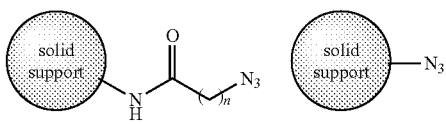

wherein n is 1, 2, 3, 4 or 5, when $X_1$ is $N_3$:

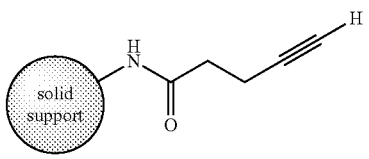

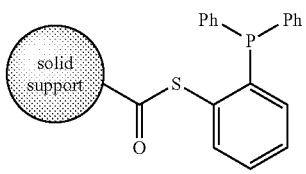

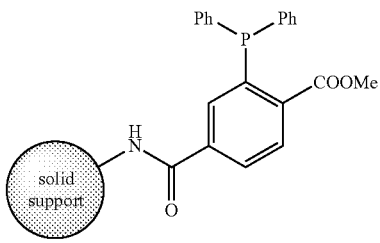

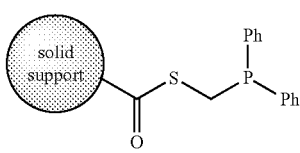

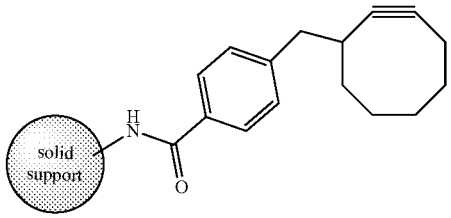

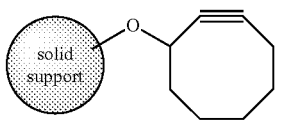

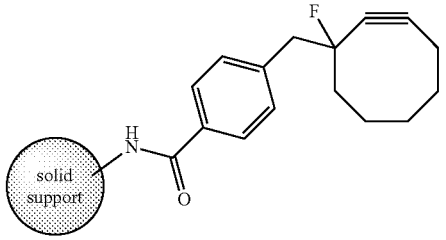

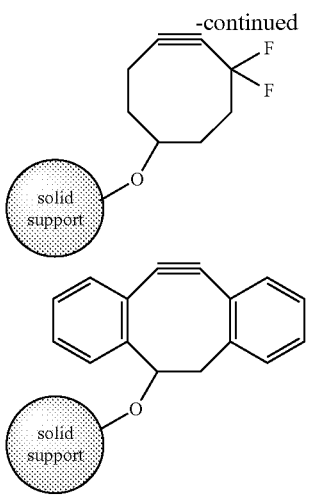

Hence, in said method for purifying a peptide produced by solid phase synthesis according to the invention, said step (d) of contacting the peptides obtained from step (c) with a solid support capable of reacting with $X_1$, depends on the nature of $X_1$ and on the nature of the solid support.

In one embodiment, when the solid support is grafted with a compound comprising an azide or an alkyne function said step (d) of the method according to the invention is performed in the presence of a catalyst, particularly selected from copper salts, typically a Cu(I) salt. In another embodiment, when the solid support is grafted with a compound comprising a cyclooctyne or a phosphine function said step (d) of the method according to the invention is performed without catalyst. Said step (d) of the method for purifying a peptide produced by solid phase synthesis according to the invention is typically performed by:

i. when $X_1$ is C≡CH:

Mixing the crude peptide mixture with an excess of azide-functionalized solid support (typically 1.2-2 molar equivalents) in an oxygen-free atmosphere, in a water based buffer at pH=5-8 (typically a 100 mM phosphate or HEPES, pH=7), optionally with the addition of an organic solvent when the peptide is not soluble in the buffer, then adding a source of Cu (I) ions (typically 0.1-10 molar equivalents) and optionally a Cu(I) ligand such as tris[(benzyl-1H-1,2,3-triazol-4-yl)methyl]amine or tris[(3-hydroxy-1-propyl-1H-1,2,3-triazol-4-yl)methyl]amine. Typically, the copper (I) source is either a solid Cu (I) salt such as copper bromide, or is obtained by extemporaneous reduction of a Cu(II) salt such as copper sulfate with a reducing agent such as sodium ascorbate or tris-(carboxyethyl)-phosphine.

ii. when $X_1$ is $N_3$:

ii. a) Mixing the crude peptide mixture with an excess of alkyne-functionalized solid support (typically 1.2-2 molar equivalents) in an oxygen-free atmosphere, in a water based buffer at pH=5-8 (typically a 100 mM phosphate or HEPES, pH=7), optionally with the addition of an organic solvent when the peptide is not soluble in the buffer, then adding a source of Cu (I) ions (typically 0.1-10 molar equivalents) and optionally a Cu(I) ligand such as tris[(benzyl-1H-1,2,3-triazol-4-yl)methyl]amine or tris[(3-hydroxy-1-propyl-1H-1,2,3-triazol-4-yl)methyl]amine. Typically, the copper (I) source is either a solid Cu (I) salt such as copper bromide, or is obtained by extemporaneous reduction of a Cu(II) salt such as copper sulfate with a reducing agent such as sodium ascorbate or tris-(carboxyethyl)-phosphine.

ii. b) Alternatively, the formation of the covalent bond with the solid support can be performed through a copper-free cycloaddition using an appropriate cyclooctyne-functionalized resin. Typically, this is performed by mixing the crude peptide mixture with an excess of cyclooctyne-functionalized solid support (typically 1.2-2 molar equivalents), in a water based buffer at pH=2-8 (typically a 100 mM phosphate or HEPES, pH=7), optionally with the addition of an organic solvent when the peptide is not soluble in the buffer.

ii. c) Still alternatively, the formation of the covalent bond with the solid support can be performed through a Staudinger ligation reaction using an appropriate phosphine-functionalized resin. Typically, this is performed by mixing the crude peptide mixture with an excess of phosphine-functionalized solid support (typically 1.2-2 molar equivalents) in an oxygen-free atmosphere, in a water based buffer at pH=5-8 (typically a 100 mM phosphate or HEPES, pH=7), optionally with the addition of an organic solvent when the peptide is not soluble in the buffer.

In said step (d), the organic solvents that can be used as additives to completely dissolve the crude peptide mixture are typically selected from the group comprising dimethylformamide, dimethylsulfoxide, N-methylpyrrolidinone, acetonitrile, hexafluoroisopropanol, trifluoroethanol, isopropanol, ethanol or methanol.

According to the invention, said step (e) of washing the solid phase support obtained from step (d) to remove immature end-capped peptides, is typically performed by transferring the solid support in an open recipient equipped with a filter able to retain the solid support but leave any solvent go freely through it, such as a polypropylene syringe fitted with a polypropylene frit or a sintered glass funnel, then flow washing successively with large volumes of different aqueous solutions and organic solvents, such as for example EDTA disodium salt 250 mM, methanol, dimethylformamide and de-ionized water.

According to the invention, said step (f) of obtaining purified mature peptides by liberating the mature peptide from the solid support by cleaving the covalent bond between $X_2$ and the mature peptides is performed under different conditions depending on the nature of the compound of general formula (I) which has been used for tagging the mature peptides. Indeed, the stability of the bond formed between the N-terminal amino group of the mature peptides and the $X_2$ moiety of said compound (I) will be different depending on the nature of $X_2$:

the bond formed between the N-terminal amino group of the mature peptides and an $X_2$ moiety of formula (A) is cleavable under nucleophilic conditions. Typically, said nucleophilic conditions according to the invention are treatment with a large excess of hydrazine, ethanolamine or hydroxylamine in a solvent such as water, or mixture of water with an organic solvent such as for example methanol, ethanol, hexafluoroisopropanol, trifluoroethanol, dimethylformamide, N-methylpyrrolidinone or acetonitrile;

the bond formed between the N-terminal amino group of the mature peptides and an $X_2$ moiety of formula (B) is cleavable under alkaline conditions. Typically, said alkaline conditions according to the invention consist of a treatment of the solid phase support with an alkaline solution having a pH greater than 9, typically between 9 and 13, particularly between 10 and 12, more particularly between 11 and 12. Suitable alkaline solutions according to the invention are CAPS buffers, phosphate buffer, or sodium hydroxide-based solutions;

the bond formed between the N-terminal amino group of the mature peptides and an $X_2$ moiety of formula (C) is cleavable under UV irradiation. Typically, said UV irradiation according to the invention consists of exposing the solid support in suspension in oxygen-free deionised water in a UV-transparent vessel to UV light at a fixed wavelength, typically 254 nm, 320 nm, 350 nm or 420 nm.

After this step (f), the mature peptide is separated from the solid support through filtration and washing of the resin with deionised water.

For $X_2$ moieties of formula (A) and (B) an alkaline solution of pure mature peptides is generally obtained. If required, it is then possible to decrease the pH of the solution with an appropriate acidifying buffer.

The invention still relates to the use of a compound having general formula (I) according to the invention for purifying a peptide produced by solid-phase synthesis.

Throughout the description of the invention, and for simplifying the representation of the molecules, a ∿∿∿ bond is used. This bond only represents the remainder(s) of the compound which is (are) not represented.

Further aspects and advantages of this invention will be disclosed in the following figures and examples, which should be regarded as illustrative and not limiting the scope of this application.

EXAMPLES

Solid-Phase Peptide Synthesis

Solid-phase peptide synthesis (SPPS) of the 31-53 fragment of the 97 amino acids protein mitogaligin (said 31-53 fragment of mitogaligin has the following amino acid sequence RGLSWTGTSRRLPWSTWSLSRST, as shown in SEQ ID NO:1) was run on an automated synthesizer 433A from Applied Biosystem using Fmoc/tBu chemistry at a 0.1 mmol scale with HBTU/HOBt as coupling reagents and a Rink resin. The elongation was carried out automatically using a 10-fold excess of protected amino acids and coupling reagents. The side-chain protecting groups used were Arg (Pbf), Ser(tBu), Thr(tBu), Trp(Boc). The 0.1 mmol scale program purchased from the manufacturer was used, with a single coupling followed by capping with acetic anhydride. A double coupling was performed for the introduction of Arg40 and Arg41. The crude peptide was released from the resin with TFA/$H_2O$/iPr$_3$SiH/phenol, 87.5/5/2.5/5 for 2 h, and the peptide was precipitated with ice-cold diethyl ether, recovered by centrifugation and washed 3 times with diethyl ether.

Figure 5:
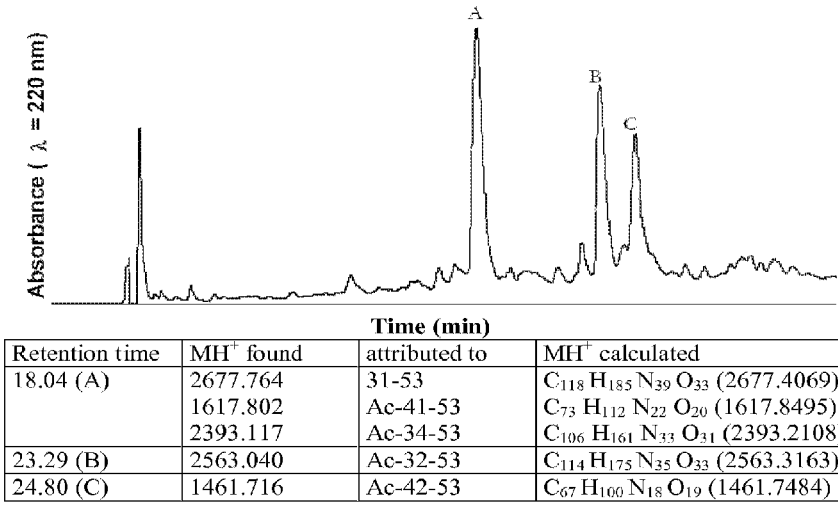
FIG. 5: HPLC-MS analysis of the crude peptides obtained after the solid-phase peptide synthesis of the 31-53 fragment of mitogaligin (mature peptide 31-53 eluted in peak A).
Figure 6:
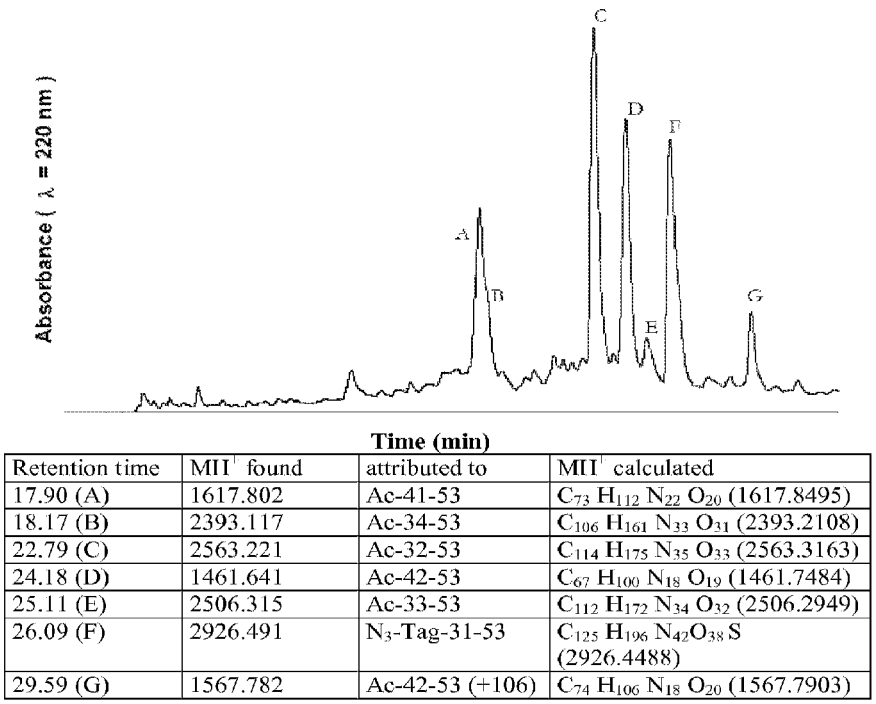
FIG. 6: HPLC-MS analysis of the peptides after tagging with the compound according to the invention (tagged mature peptide 31-53 eluted in peak F).
Figure 7:
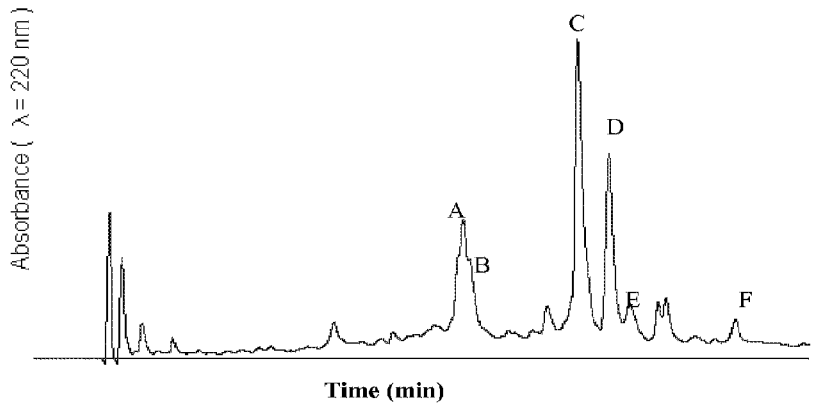
FIG. 7: HPLC-MS analysis of the crude cycloaddition mixture (t=2 h) showing the total consumption of the tagged mature peptide 31-53.
Figure 8:
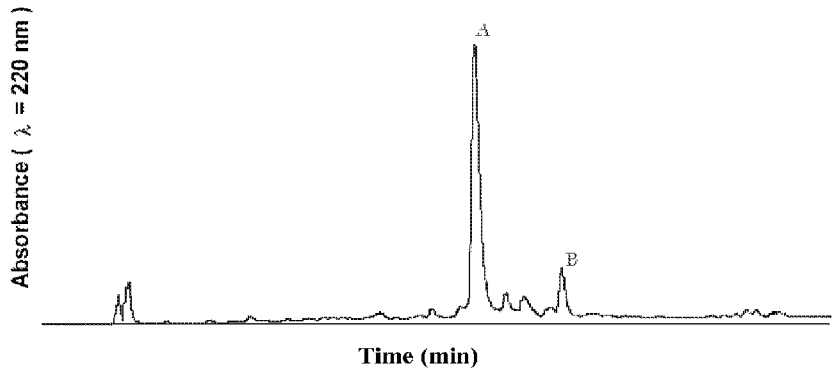
FIG. 8: HPLC-MS analysis after wash of the resin, then mild base-mediated release.

The peptides were analyzed by HPLC (high pressure liquid chromatography) and MALDI-TOF (Matrix Assisted Laser Desorbtion Ionization/Time of Flight) mass spectrometry (FIG. 5-8). HPLC analyses were carried out on the LaChrom Elite system equipped with a Hitachi L-2130 pump, a Hitachi L-2455 diode array detector and a Hitachi L-2200 autosampler. The machines were equipped with C18 reversed-phase columns, Nucleosil, 300 Å, 5 µm, 250×4.6 mm. Solvents A and B were 0.1% TFA in $H_2O$ and 0.1% TFA in MeCN, respectively. The gradient was 25% to 35% B over 30 min at a flow rate of 1 ml/min. MS analyses were performed on an Autoflex MALDI-TOF instrument (Bruker Daltonics, Bremen, Germany) equipped with a 337-nm nitrogen laser and a gridless delayed extraction ion source. The instrument was used in reflector positive ion mode with a 150 ns delay and an accelerating voltage of 19 kV. Instrument control and external calibration were accomplished using Flex-Control software (Bruker). The observed m/z correspond to the monoisotopic ions. The sample was co-crystallized with a solution of α-cyano-4-hydroxy-cinnamic acid (HCCA) as a matrix, using the dry droplet method. The mature peptide (31-53) was eluted in peak A, as shown in FIG. 5.

Figure 1:
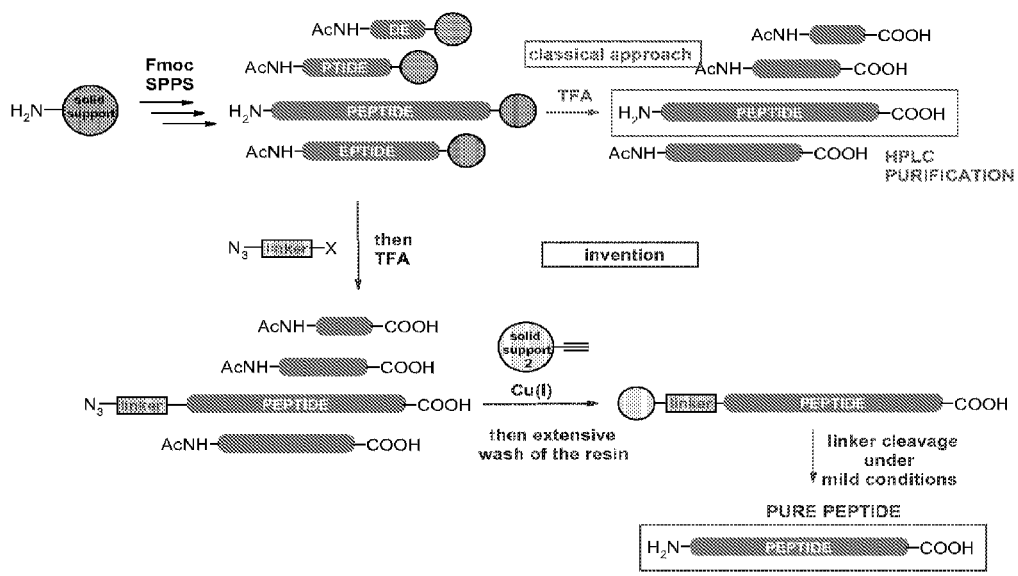
FIG. 1: General principle of the invention.
Figure 2:
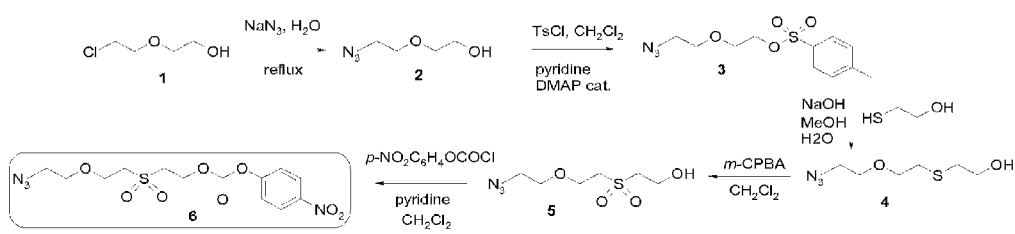
FIG. 2: Synthesis of the activated carbonate 6.
Figure 3:
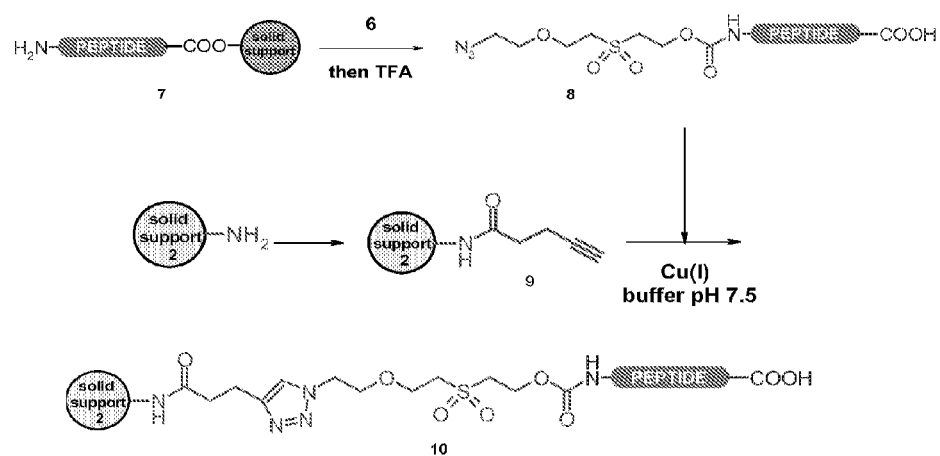
FIG. 3: Selective grafting on the solid support by copper (I)-catalyzed cycloaddition.
Figure 4:
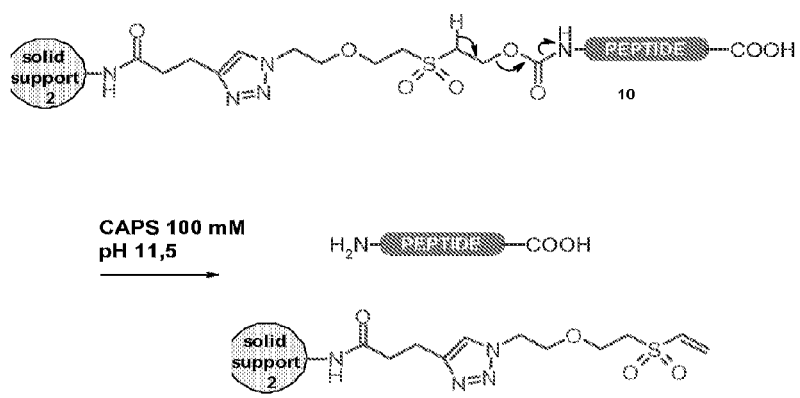
FIG. 4: Final cleavage from the second resin.

Synthesis of the Activated Carbonate 6 (FIG. 2)

2-(2-Azido-Ethoxy)-Ethanol (2)

A solution of 2-(2-chloro-ethoxy)-ethanol (15 g, 0.12 mol) and sodium azide (15.7 g, 2 equiv.) in $H_2O$ (50 ml) was heated at 90° C. for 16 h. The reaction mixture was cooled down to RT then extracted with $CH_2Cl_2$ (6×50 ml). The combined organic layers were dried over $MgSO_4$ and filtrated. The solvents were removed under reduced pressure to give azide 2 as a colorless liquid (15 g, 95%). $^1H$ and $^{13}C$ NMR spectra matched the literature data (Cheng, H. et al. *J. Med. Chem.* 2005, 48, 645-653).

$^1H$ NMR (500 MHz, $CDCl_3$): δ 3.78-3.73 (m, 2H), 3.70 (t, 2H, J=5.0 Hz), 3.61 (t, 2H, J=4.5 Hz), 3.41 (t, 2H, J=5.0 Hz), 2.09 (bt, 1H); $^{13}C$ NMR (125 MHz, $CDCl_3$): δ 72.7, 70.3, 62.1, 51.0.

Toluene-4-Sulfonic Acid 2-(2-Azido-Ethoxy)-Ethyl Ester (3)

A solution of 2-(2-azido-ethoxy)-ethanol 2 (14.1 g, 0.108 mol) and pyridine (13 ml, 1.5 equiv.) in $CH_2Cl_2$ (150 ml) was cooled in an ice bath. p-Toluenesulfonyl chloride (30.7 g, 1.5 equiv.) then DMAP (173 mg, 0.01 equiv.) were added. The reaction mixture was stirred at RT for 72 h, then washed with a 1 M HCl aqueous solution (3×50 ml), dried over $MgSO_4$, filtrated then concentrated under reduced pressure. Purification by flash column chromatography (eluent: pet. ether/AcOEt 9:1 then 7:3) afforded tosylate 3 as a colorless oil (23.8 g, 78%). $^1H$ and $^{13}C$ NMR spectra matched the literature data (Gill, H. et al. *J. Med. Chem.* 2009, 52, 5816-5825).

$^1H$ NMR (500 MHz, $CDCl_3$): δ 7.81 (d, 2H, J=8.2 Hz), 7.35 (d, 2H, J=8.2 Hz), 4.17 (t, 2H, J=4.7 Hz), 3.70 (t, 2H, J=4.7 Hz), 3.61 (t, 2H, J=5.0 Hz), 3.32 (t, 2H, J=5.0 Hz), 2.45 (s, 3H); $^{13}C$ NMR (125 MHz, $CDCl_3$): δ 145.2, 133.2, 130.1, 128.2, 70.4, 69.4, 69.0, 50.9, 21.9.

2-[2-(2-Azido-Ethoxy)-Ethylsulfanyl]-Ethanol (4)

Aqueous NaOH (3.33 g in 20 ml $H_2O$, 1.5 equiv.) was added dropwise to a solution of tosylate 3 (15.8 g, 55.5 mmol)

and β-mercaptoethanol (5.8 ml, 1.5 equiv.) in MeOH (200 ml). The resulting mixture was stirred at RT for 72 h then methanol was evaporated under reduced pressure. The resulting suspension was diluted with water (50 ml) and extracted with $CH_2Cl_2$ (6×50 ml). The combined organic layers were dried over $MgSO_4$, filtrated then concentrated under reduced pressure. Purification by flash column chromatography (eluent: pet. ether/AcOEt 8:2 then 6:7) afforded sulfide 4 as a colorless liquid (8.41 g, 79%).

$^1H$ NMR (500 MHz, $CDCl_3$): δ 3.74 (t, 2H, J=5.8 Hz), 3.68 (t, 2H, J=6.4 Hz), 3.65 (t, 2H, J=5.0 Hz), 3.40 (t, 2H, J=5.0 Hz), 2.79 (t, 2H, J=5.8 Hz), 2.75 (t, 2H, J=6.4 Hz), 2.41 (bs, 1H); $^{13}C$ NMR (125 MHz, $CDCl_3$): δ 71.4, 69.9, 60.9, 50.9, 36.2, 31.5; ESI-HRMS: $[M+H]^+$ m/z=214.0623 (calcd for $C_6H_{13}N_3NaO_2S$: 214.0626).

2-[2-(2-Azido-Ethoxy)-Ethylsulfonyl]-Ethanol (5)

A solution of sulfide 3 (8.41 g, 44 mmol) in $CH_2Cl_2$ (100 ml) was cooled in an ice bath. mCPBA (84% purity, 27.1 g, 3 equiv.) was added portion wise and the resulting solution was stirred at RT for 16 h. An aqueous 1 M $NaHSO_3$ solution (20 ml) was added, and the resulting suspension was vigorously stirred at RT for 30 min. The white m-chlorobenzoic acid precipitate was filtrated over a celite pad. The organic layer was washed with a saturated aqueous $NaHCO_3$ solution (3×20 ml), dried over $MgSO_4$, filtrated then concentrated under reduced pressure. Purification by flash column chromatography (eluent: pet. ether/AcOEt 1:1 then 3:7 then pure AcOEt) afforded sulfone 5 as a colorless liquid (8.41 g, 86%).

$^1H$ NMR (500 MHz, $CDCl_3$): δ 4.12 (t, 2H, J=5.1 Hz), 3.96 (t, 2H, J=5.3 Hz), 3.67 (t, 2H, J=4.9 Hz), 3.44 (t, 2H, J=4.9 Hz), 3.34-3.40 (m, 4H), 2.63 (bs, 1H); $^{13}C$ NMR (125 MHz, $CDCl_3$): δ 70.2, 65.2, 57.5, 56.7, 55.0, 51.0; ESI-HRMS: $[M+Na]^+$ m/z=246.0519 (calcd for $C_6H_{13}N_3NaO_4S$: 246.0524).

2-[2-(2-Azido-Ethoxy)-Ethylsulfonyl]-Ethyl 4-Nitrophenyl Carbonate (6)

A solution of alcohol 5 (4.0 g, 17.9 mmol) and pyridine (10 ml, 6.9 equiv.) in $CH_2Cl_2$ (100 ml) was cooled in an ice bath and p-nitrophenyl chloroformate (5.42 g, 1.5 equiv.) was added. The resulting solution was stirred at RT for 16 h then washed with a 1 M HCl aqueous solution (3×50 ml), dried over $MgSO_4$, filtrated then concentrated under reduced pressure. Purification by flash column chromatography (eluent: pet. ether/AcOEt 7:3 then 1:1) afforded carbonate 6 as a white amorphous solid (6.3 g, 91%).

$^1H$ NMR (500 MHz, $CDCl_3$): δ 8.29 (d, 2H, J=8.8 Hz), 7.40 (d, 2H, J=8.8 Hz), 4.75 (t, 2H, J=5.8 Hz), 3.97 (t, 2H, J=5.1 Hz), 3.68 (t, 2H, J=4.6 Hz), 3.61 (t, 2H, J=5.8 Hz), 3.43 (t, 2H, J=4.6 Hz), 3.35 (t, 2H, J=5.1 Hz); $^{13}C$ NMR (125 MHz, $CDCl_3$): δ 155.5, 152.2, 145.8, 125.6, 122.0, 70.3, 65.2, 62.2, 55.1, 53.9, 50.9; ESI-HRMS: $[M+Na]^+$ m/z=411.0581 (calcd for $C_{13}H_{16}NaN_4O_8S$: 411.0587).

On-Resin Installation of the Azido Traceless Tag

The activated carbonate $N_3$—$CH_2CH_2OCH_2CH_2SO_2CH_2CH_2$—OCOO-(pNO$_2$)—$C_6H_4$ 6 (10 equiv.) dissolved in DMF in the presence of $iPr_2NEt$ (20 equiv) was mixed with the peptide resin 7 (1 equiv) for 2 h. The peptide resin was then washed with DMF (3×) and $CH_2Cl_2$ (3×), and a standard TFA cleavage was applied to release the azido-tagged peptide 8 (HPLC peak F, see FIG. 6).

Selective Loading of the Azido-Tagged Peptide on an Alkyne Resin

Aminomethyl PEGA 800 resin (Novabiochem) at 0.4 mmol/g (1 equiv.) was introduced in a syringe equipped with a polypropylene frit and a teflon tap and washed successively with $CH_2Cl_2$ (3×), 0.1% TFA in $CH_2Cl_2$ (3×), $CH_2Cl_2$ (3×), 10% $iPr_2NEt$ in $CH_2Cl_2$ (3×), $CH_2Cl_2$ (3×) and peptide synthesis-grade DMF (3×). Then, pentynoic acid (2 equiv.) and HATU (2 equiv.) were transferred by suction followed by the transfer of $iPr_2Net$ (4 equiv.). The resin was mixed by rotation for 2 h. The completion of the reaction was checked using Kaiser's test. After thoroughly washing with DMF (3×), $CuSO_4$ (0.5 equiv.) and Na ascorbate (1 equiv.) dissolved in deoxygenated 100 mM HEPES buffer pH 7, were added to the alkyne resin 9 (2 equiv.) followed by the addition of the crude azido-tagged peptide 8 (1 equiv.). After 2 h, the supernatant was checked by HPLC for the total consumption of the tagged peptide 8 (see FIG. 7) and the peptide resin 10 was thoroughly washed with a 250 mM EDTA disodium salt solution (pH 4.2), de-ionized water, methanol, dimethylformamide and de-ionized water, successively, to eliminate truncated peptides and copper catalyst.

Release of the Pure, Untagged Target Peptide

The peptide resin 10 was finally treated with 50 mM CAPS buffer, pH 11.7, (2×30 min) at 20° C., or 3×5 min at 37° C. (see HPLC analysis in FIG. 8), and the solution was acidified with TFA down to pH 3-5. Buffer salts can subsequently be removed using standard procedures such as hydrophobic SPE cartridge.

Throughout this application, various references describe the state of the art to which this invention pertains. The disclosures of these references are hereby incorporated by reference into the present disclosure.

The invention claimed is:

1. A compound having general formula (I):

$$X_1\text{-}L\text{-}X_2 \quad (I)$$

wherein:
X$_1$ is selected from the group consisting of —N$_3$ or —C≡CH,
L represents a linker separating X$_1$ and X$_2$,
X$_2$ is selected from the group consisting of the compounds having general formula (A), and the compounds having general formula (C):

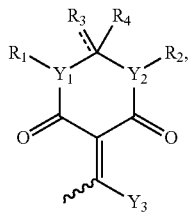

(A)

wherein:
Y$_1$ and Y$_2$ independently represent —CH— or —N—,
Y$_3$ represents —OH or a leaving group,
R$_1$ and R$_2$ independently represent —H, —CH$_3$, or a C$_2$-C$_5$ alkyl,
the dotted line to R$_3$ represents an optional double bond wherein,
when the double bond is present, R$_3$ is O and R$_4$ is absent,
when the double bond is not present, R$_3$ and R$_4$ represent —CH$_3$; and

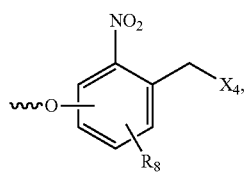

(C)

wherein the compounds of general formula (C) are:

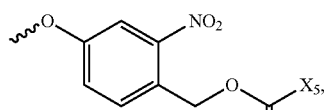

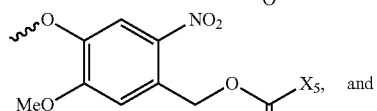

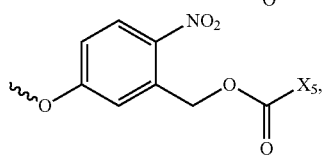

wherein X$_5$ is a leaving group.

2. The compound according to claim 1, wherein said linker L separates X$_1$ and X$_2$ by at least one atom, particularly by 1 to 30 consecutive atoms.

3. The compound according to claim 1, wherein said linker L is selected from the group comprising —(CH$_2$)$_n$—, —CH$_2$—(CH$_2$—O—CH$_2$)$_n$—CH$_2$—, —Ar—, —(CH$_2$)$_n$—Ar—, —CH$_2$—(CH$_2$—O—CH$_2$)$_n$—CH$_2$—Ar—, —(CH$_2$)$_n$—O—Ar—, —CH$_2$—(CH$_2$—O—CH$_2$)$_n$—CH$_2$—O—Ar— and —CH$_2$—(CH$_2$—O—CH$_2$)$_n$—Ar—, wherein "n" is 1, 2, 3, 4, 5, 6, 7, 8, 9, 10 or more, and wherein Ar represents an aryl group having the following formula:

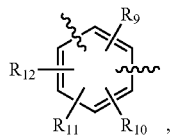

wherein R$_9$, R$_{10}$, R$_{11}$ and R$_{12}$ independently represent H, —CH$_3$, —O—CH$_3$, —NO$_2$, or an halogen atom.

4. The compound according to claim 1, wherein said compound of general formula (A) is selected from the group comprising:

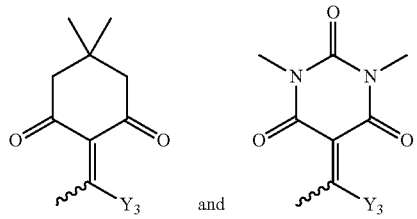

wherein Y$_3$ represents —OH or a leaving group.

5. The compound according to claim 1, wherein when Y$_3$ is a leaving group, Y$_3$ is selected from the group comprising —OR$_{13}$ and N(R$_{13}$)$_2$, wherein R$_{13}$ represents CH$_3$ or a C$_2$, C$_3$, C$_4$ or C$_5$ alkyl.

6. A method for purifying a peptide produced by solid-phase synthesis, said method comprising the steps of:
(a) obtaining a mixture of mature peptides having a free N-terminal amino group and immature end-capped peptides, wherein said mature and immature peptides have their side chains protected and are covalently bound to a solid phase;
(b) contacting the mixture of step (a) with the compound of claim 1,
wherein said step of contacting the mixture obtained from step (a) with a compound having general formula (I) results in the formation of a covalent link between the mature peptide and the compound having general formula (I) by reaction of the free N-terminal amino group of the mature peptide with X$_2$,
(c) subjecting the mixture obtained from step (b) to an acid treatment to cleave the peptides from the solid phase,
(d) contacting the peptides obtained from step (c) with a solid support that reacts with X$_1$, said step resulting in the formation of a stable covalent bond between the solid support and the mature peptides,
(e) washing the solid support obtained from step (d) to remove immature end-capped peptides,
(f) obtaining purified mature peptides by liberating them from the solid support by cleaving the covalent bond between X$_2$ and the mature peptides under a condition selected from the group consisting of:
  i. nucleophilic condition when X$_2$ is (A),
  ii. alkaline condition when X$_2$ is (B), and
  iii. UV irradiation when X$_2$ is (C).

7. The method according to claim 6, wherein said solid support is grafted with a compound, wherein said compound comprises an azide, an alkyne, a cyclooctyne or a phosphine function capable of reacting with $X_1$.

8. The method according to claim 6, wherein said solid support is selected from the group comprising:

when $X_1$ is C≡CH:

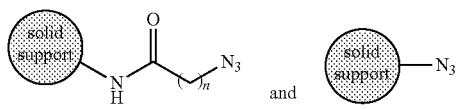

wherein n is 1, 2, 3, 4 or 5,
when $X_1$ is $N_3$:

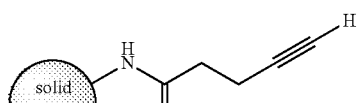

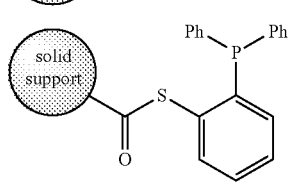

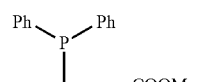

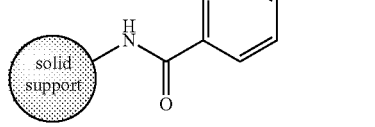

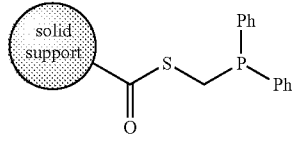

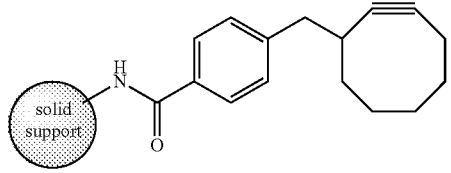

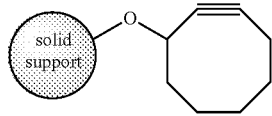

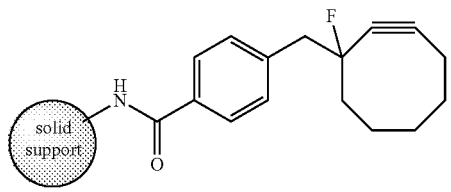

-continued

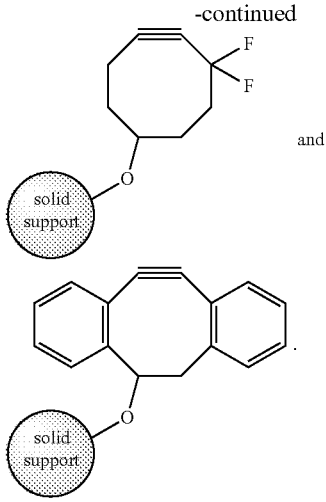

9. The compound according to claim 2, wherein said linker L is selected from the group comprising —$(CH_2)_n$—, —$CH_2$—$(CH_2$—O—$CH_2)_n$—$CH_2$—, —Ar—, —$(CH_2)_n$—Ar—, —$CH_2$—$(CH_2$—O—$CH_2)_n$—$CH_2$—Ar—, —$(CH_2)_n$—O—Ar—, —$CH_2$—$(CH_2$—O—$CH_2)_n$—$CH_2$—O—Ar— and —$CH_2$—$(CH_2$—O—$CH_2)_n$—Ar—, wherein "n" is 1, 2, 3, 4, 5, 6, 7, 8, 9, 10 or more, and wherein Ar represents an aryl group having the following formula:

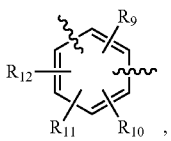

wherein $R_9$, $R_{10}$, $R_{11}$ and $R_{12}$ independently represent H, —$CH_3$, —O—$CH_3$, —$NO_2$, or an halogen atom.

10. The method according to claim 7, wherein said solid support is selected from the group comprising:

when $X_1$ is C≡CH:

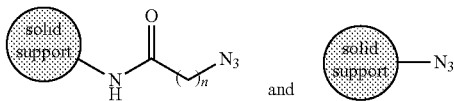

wherein n is 1, 2, 3, 4 or 5,
when $X_1$ is $N_3$:

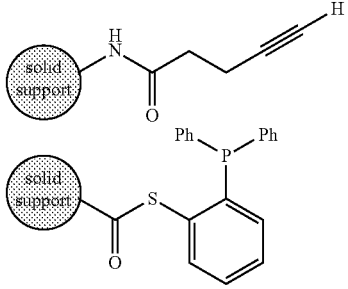

21
-continued
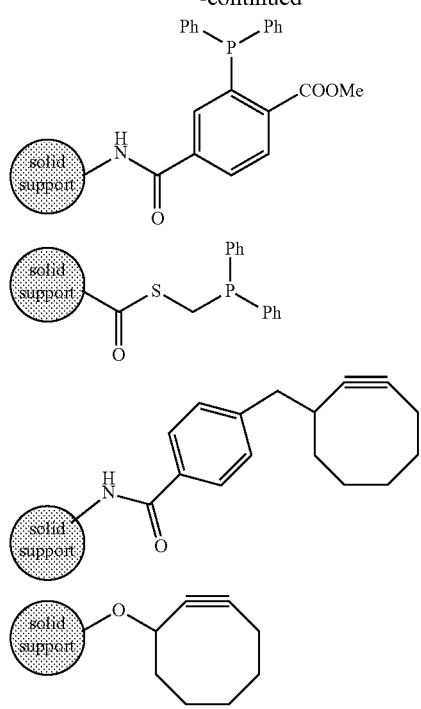
22
-continued
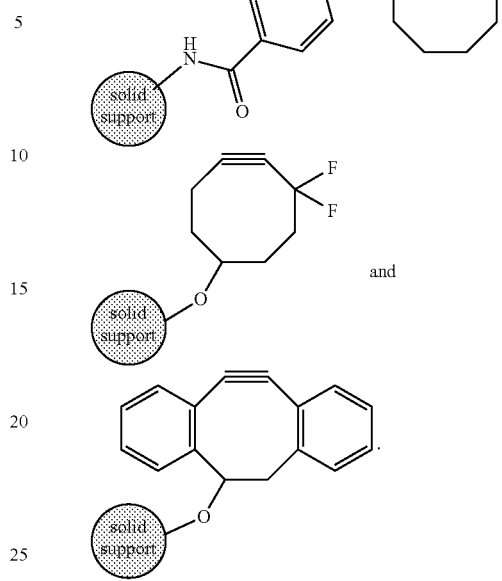
and
* * * * *